Figure 1A:
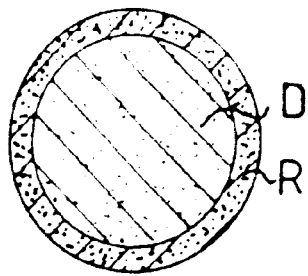

United States Patent

Bauer et al.

[11] Patent Number: 6,086,919
[45] Date of Patent: Jul. 11, 2000

[54] PHARMACEUTICAL COMPOSITION CONTAINING THE ACE INHIBITOR RAMIPRIL AND A DIHYDROPYRIDINE COMPOUND

[75] Inventors: Brigitte Bauer, Darmstadt, Germany; Christer Karlsson, Lindome, Sweden; Per Johan Lundberg, Mölndal, Sweden; Berit Nilsson, Göteborg, Sweden; Anders Sandberg, Mölndal, Sweden; Alfred Sickmüller, Frankfurt/M, Germany

[73] Assignee: Astra Aktiebolag, Sodertalje, Sweden

[21] Appl. No.: 08/522,267

[22] PCT Filed: Aug. 30, 1995

[86] PCT No.: PCT/SE95/00972

§ 371 Date: Sep. 12, 1995

§ 102(e) Date: Sep. 12, 1995

[87] PCT Pub. No.: WO96/07400

PCT Pub. Date: Mar. 14, 1996

[30] Foreign Application Priority Data

Sep. 2, 1994 [SE] Sweden .................................. 9402924
Sep. 2, 1994 [SE] Sweden .................................. 9402925

[51] Int. Cl.[7] ...................................................... A61R 9/14
[52] U.S. Cl. ........................... 424/489; 424/468; 424/473; 424/472; 424/451
[58] Field of Search .................................. 424/489, 464, 424/465, 472, 473, 451, 468

[56] References Cited

U.S. PATENT DOCUMENTS 3,644,627  2/1972  Friedrich .
4,703,038  10/1987 Bernward et al. .
4,743,450  5/1988  Harris et al. .
4,857,520  8/1989  Urbach et al. .
5,151,433  9/1992  Fulbreth et al. .
5,160,744  11/1992 Jao et al. .
5,178,867  1/1993  Guittard et al. ......................... 424/473
5,236,933  8/1993  Becker et al. .

FOREIGN PATENT DOCUMENTS 2070085   12/1992  Canada .
0007293   6/1982   European Pat. Off. .
0158927   10/1985  European Pat. Off. .
0265685   9/1987   European Pat. Off. .
0288732   11/1988  European Pat. Off. .
0317878   11/1988  European Pat. Off. .
0508511   10/1992  European Pat. Off. .
1358951   7/1974   United Kingdom .
2164336   3/1986   United Kingdom .
WO9628185 9/1996   WIPO .

OTHER PUBLICATIONS

Br. J. Clin. Pharmac., vol. 36, (1993), pp. 323–330.

*Primary Examiner*—Thurman K. Page
*Assistant Examiner*—William E. Benston, Jr.
*Attorney, Agent, or Firm*—White & Case LLP

[57] ABSTRACT

The invention is directed to a pharmaceutical composition which is a combination of the ACE inhibitor ramipril and a calcium antagonist of one of the dihydropyridine type compounds felodipine, nitrendipine, nifedipine and lacidipine. The pharmaceutical composition is for use in the therapy and treatment of hypertension.

39 Claims, 1 Drawing Sheet

PHARMACEUTICAL COMPOSITION CONTAINING THE ACE INHIBITOR RAMIPRIL AND A DIHYDROPYRIDINE COMPOUND

This Application is a 371 of PCT/SE95/00792 filed Aug. 30, 1995.

FIELD OF THE INVENTION

The present invention being a new pharmaceutical composition is related to a novel pharmaceutical preparation for oral administration and the use of this pharmaceutical preparation in the therapy of hypertension and of diseases in the cardiovascular system and secondary effects thereof in mammals including man. It is also related to compositions and to methods of preparing said pharmaceutical preparations. The pharmaceutical preparation is a fixed unit dosage form of the long-acting angiotensin converting enzyme (ACE) inhibitor, ramipril, in instant release form and a calcium antagonist of the dihydropyridine type i.e. a calcium channel blocking agent (dihydropyridine compound) in an extended release formulation.

The present invention also relates to solid preparations which are fixed combinations of the long acting ACE inhibitor ramipril in instant release form and a dihydropyridine compound such as the vascular selective drug felodipine in extended release form having the characteristic of achieving an effect over 24 hours after once daily administration. The pharmaceutical preparations of the present invention retain a good therapeutic effect in the treatment of hypertension even when the active drugs are administered in low doses. The pharmaceutical preparations reduce the dose related adverse events which result from administering higher doses of each of the drugs separately. The pharmaceutical preparations of this invention simplify the regimen and improve patient compliance.

BACKGROUND OF THE INVENTION

ACE inhibitors are compounds which inhibit the conversion of angiotensine I into the active angiotensine II as well as the breakdown of the active vasodilator bradykinin. Both of these mechanisms lead to vasodilation. Such compounds have been described in, for example, EP 158927, EP 317878, U.S. Pat. No. 4,743,450, and U.S. Pat. No. 4,857,520. Ramipril (disclosed in EP 079022) is a long-acting ACE inhibitor. Its active metabolite is the free acid ramiprilat, which is obtained in vivo upon administration of ramipril. In hypertensive patients administration of ramipril is known to cause a reduction in peripheral arterial resistance and thus a reduction of the blood pressure without a compensatory rise in heart rate. It is being used in the treatment of hypertension and congestive heart failure. Furthermore, ramipril has been shown to reduce mortality in patients with clinical signs of congestive heart failure after surviving an acute myocardial infarction. Ramipril has been suggested to have an added advantage over many other ACE inhibitors due to its pronounced inhibition of ACE in tissues resulting in organ protective effects in e.g. the heart, lung, and kidney.

Ramipril substance is sensitive to high temperature, moisture or compression and therefore, upon formulation into pharmaceutical preparations needs special attention in order to retain its stability (U.S. Pat. No. 5,151,433).

Calcium antagonists are compounds which influence the inflow of calcium ions into cells, in particular into the cells of smooth muscles. Such compounds of the dihydropyridine type have been described in, for example, GB 1358951 (nitrendipine), U.S. Pat. No. 3,644,627 (nifedipine), EP 007293 (felodipine), and GB 2164336 (lacidipine).

The most common adverse events which are observed in clinical use of the ACE inhibitor and the calcium antagonists of this invention are headache, coughing, peripheral oedema, flush, dizziness, fatigue and nausea.

Some dihydropyridines, for example nifedipine and felodipine are decomposed when exposed to light, and therefore, upon handling and formulation into pharmaceutical preparations need special attention in order to retain their stability.

Combinations of ACE inhibitors and calcium antagonists of dihydropyridine type in the treatment of hypertension have been described in, for example EP 488059, EP 180785 and EP 265685.

Bainbridge, A.D. et al. (Br. J. Clin. Pharmac. 1993, 36: 323–330) have studied the use of the angiotensin converting enzyme inhibitor ramipril and an extended release formulation of the dihydropyridine calcium channel antagonist felodipine given in free combination as separate dosage forms.

In U.S. Pat. No. 4,703,038 solid combinations for oral administration of certain ACE inhibitors and certain dihydropyridine compounds including i.a. nitrendipine and felodipine are described. This document also describes a method of treating hypertension in man using such combinations. U.S. Pat. No. 4,703,038 does not, however, disclose ramipril as an ACE inhibitor. Neither does it describe the use of extended release formulations of dihydropyridines.

In U.S. Pat. No. 5,236,933 the use of combinations of certain ACE inhibitors including i.a. ramipril, and certain calcium antagonists, i.a. felodipine have been described in the prevention and/or treatment of proteinuria.

DESCRIPTION OF THE INVENTION

The term "instant release" as used herein defines the release of an active drug component that conforms with the criteria in USP XXII under entry "<711> Dissolution" when Q=75%, the time interval is 60 minutes and the dissolution medium is the one specified in Examples 5–8 below.

The term "extended release" as used herein defines the dissolution of the active drug component from the dosage form over an extended period of time, i.e. for more than 6 hours as measured with the testing method described in Examples 5–8 below.

The term "fixed unit dosage form" as used herein defines a physical embodiment containing more than one active drug component, which embodiment has a heterogenous structure.

Dose figures of pharmaceutically acceptable salts of the active drug given herein relate to the amount of the corresponding free base or acid.

The present invention provides a solid, fixed unit dosage form for oral administration, for example a tablet or a capsule, of an instant release formulation of the long acting ACE inhibitor ramipril or a pharmaceutically acceptable salt of ramipril, and an extended release preparation of a dihydropyridine selected from the group consisting of felodipine, nitrendipine, nifedipine, and lacidipine or a pharmaceutically acceptable salt thereof. Said solid, fixed unit dosage form is effective and tolerable after once daily dosing. Most preferred of the dihydropyridines is felodipine or a pharmaceutically acceptable salt thereof. The choice of an instant release formulation of the long acting ACE inhibitor ramipril and an extended release preparation of a dihydropyridine both contribute to the optimal use of both drugs thereby minimizing the adverse effects while still being effective against elevated blood pressure.

The molecule corresponding to ramipril has five chiral centers and can, thus, occur in 32 different enantiomeric forms. The enantiomer with the name (2S, 3aS, 6aS))-1-[N-[(S)- 1-(ethoxycarbonyl)-3-phenylpropyl ]-L-alanyl]-octahydro-cyclopenta[b]pyrrol-2-carboxylic acid is preferred. This compound is called ramipril.

Pharmaceutically acceptable salts of ramipril are, for example, salts with pharmaceutically acceptable amines or inorganic or organic acids such as, HCl, HBr, $H_2SO_4$, maleic acid, fumaric acid, tartaric acid and citric acid.

Felodipine has one chiral center and can, thus, occur in two different enantiomeric forms. The vasodilatory effect of the S form is stronger than the vasodilatory effect of the R form. However, both the S form and racemic mixtures of the S form and the R form can be used.

Pharmaceutically acceptable salts of felodipine can be prepared from inorganic and organic acids including for example acetic, benzene-sulfonic, benzoic, camphorsulfonic, citric, ethenesulfonic, fumaric, gluconic, glutamic, hydrobromic, hydrochloric, isethonic, lactic, maleic, malic, mandelic, methanesulfonic, mucic, nitric, pamoic, pantothenic, phosphoric, succinic, sulfuric, tartaric, and p-toluene-sulfonic acids.

An extended release formulation can, for example, be constructed to give a hydrophilic gel matrix wherein the active substance is enclosed and which upon contact with aqueous solutions will swell to permit release of the active substance by diffusion and/or attrition.

In order to prevent decomposition of ramipril substance by the action of moisture during storage or compression during the manufacturing process the substance is, according to the present invention preferably powder-coated when included in a compressed part of the dosage form. The dihydropyridine substance is light sensitive and is, therefore, protected by a coating layer.

The dose range of ramipril in the combined fixed unit dosage forms is 1–10 mg. The dose range in the combined fixed unit dosage forms is, for felodipine 1–10 mg, for nitrendipine 2–40 mg, for nifedipine 5–70 mg and for lacidipine 1–8 mg.

Most preferred dose range in the combined fixed unit dosage forms is, for ramipril 1–5 mg, for felodipine 1–5 mg, for nitrendipine 5–20 mg, for nifedipine 10–60 mg and for lacidipine 2–6 mg.

A preferred form of the present invention consists of a solid fixed unit dosage form for oral administration which is a low dose combination of an instant release formulation of 1–5 mg of the long acting ACE inhibitor ramipril or a pharmaceutically acceptable salt thereof, and an extended release formulation of 1–5 mg of the vascular selective calcium antagonist felodipine or a pharmaceutically acceptable salt thereof. Especially preferred dose intervals for this preferred form of the invention are 1–3 mg of ramipril and 1–3 mg of felodipine. The preferred dosis quotient between ramipril and felodipine in the preferred form of the present invention is 1:1.

The pharmaceutical preparations of the present invention are for once daily administration utilizing the different blood pressure lowering mechanisms of the ACE inhibitor ramipril in an instant release formulation and a dihydropyridine compound selected from the group consisting of felodipine, nitrendipine, nifedipine, and lacidipine in an extended release formulation. The bioavailability of the ramipril component of the pharmaceutical preparation according to the present invention as measured by the blood plasma concentration of ramiprilat is equivalent to that of the same component administered separately (see Example 1). Also the bioavailability of the dihydropyridine component of the pharmaceutical preparation is equivalent as measured in the same way (see Example 2). The compositions of tablets which were tested are shown in Example 12.

The use of a low dose of the two active components and the extended release of the dihydropyridine component of the pharmaceutical preparations of the present invention administered once daily give a lowering effect on blood pressure but no compensatory increase in heart rate. It is effective in the treatment of systolic as well as diastolic hypertension. The pharmaceutical preparation is particularly effective in the treatment of systolic hypertension. So administered the preparations have a beneficial influence upon conditions of and associated with high blood pressure (hypertension) in mammals including man. Examples 3 and 4 illustrate the effectiveness of the pharmaceutical preparations of the invention in comparative tests between either ramipril or felodipine and solid fixed combination dosage forms of ramipril and felodipine. It can be seen that there is a surprisingly high degree of reduction in the systolic and diastolic blood pressure of the combined low dose (2.5 mg+2.5 mg of ramipril and felodipine) preparation in the example in comparison both with each of the components in monotherapy and with the fixed combined preparation of the components in higher (5 mg+5 mg) dose.The incidence of the most common adverse events during administration of an ACE inhibitor (dizziness, headache, fatigue, nausea and coughing) are low and comparable with that of placebo. The adverse events of administration of dihydropyridine calcium antagonists (increased heart rate, flushing, peripheral oedema, headache and dizziness) are also low and comparable to placebo.

Above all it is evident from Examples 3 and 4 that the most bothersome adverse event of administration of ACE inhibitors, namely coughing, and of administration of dihydropyridine calcium antagonists, namely peripheral oedema and flushing is less common with the low dose combination compared with the monotherapies (F5 and R5).

The release of the respective components in in vitro tests can be seen in Examples 5 to 8.

The pharmaceutical preparation is formulated as a combined solid fixed unit dosage form for oral administration which in combination with the once daily administration facilitates the regimen and improves patient compliance.

The combined solid fixed unit dosage forms of the present invention can be for example capsules or tablets, which optionally can be coated.

As examples of formulations of ramipril which can be enclosed into capsules can be mentioned ramipril in the form of powder or granules, optionally attached to a carrier substance, and tablets. Examples of extended release preparations of dihydropyridine which can be enclosed into such capsules are granules or tablets. A capsule wherein the ramipril substance is attached to a carrier substance and the dihydropyridine is enclosed in a tablet core consisting of a hydrophilic gel matrix and the process for manufacturing the same is illustrated in Example 9.

Figure 1B:
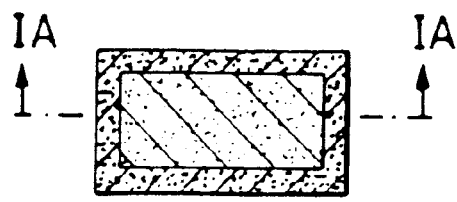
Figure 2A:
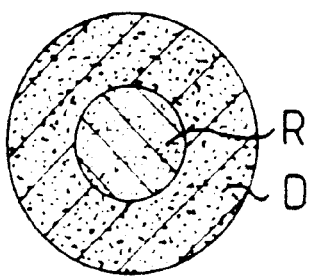
Figure 2B:
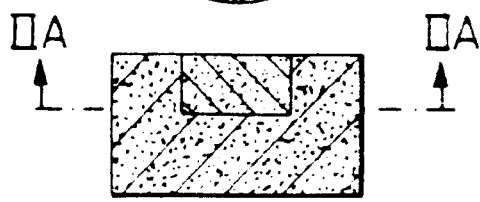
Figure 3A:
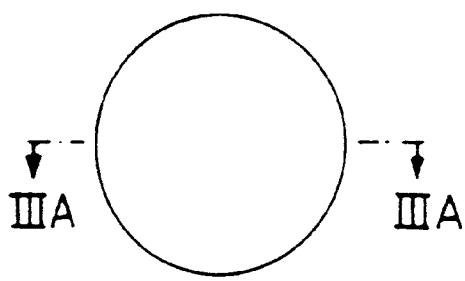
Figure 3B:
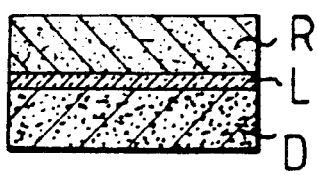

Examples of the construction of tablets as fixed unit dosage forms of ramipril and an extended release dihydropyridine portion are shown in FIGS. 1, 2 and 3.

FIG. 1 illustrates a tablet where the dihydropyridine ER (D) matrix preparation is enclosed in a surrounding layer containing instant release ramipril (R) substance. Such a tablet can be manufactured in a suitable tabletting machine. Alternatively, the matrix containing dihydropyridine can be compressed to tablets in a tabletting machine and then coated with a coating containing ramipril. One tablet of this type is illustrated in Example 10.

FIG. 2 illustrates a tablet where the ramipril (R) component is placed at the upper part of the matrix containing the dihydropyridine ER (D) preparation. The instant release ramipril component is contained in a smaller part which is enclosed in a larger, separate part containing the felodipine extended release preparation. Instant release of ramipril is achieved since it is not entirely enclosed in the matrix. Such a tablet can be manufactured in a suitable tabletting machine.

FIG. 3 illustrates a tablet which is composed of one tablet layer containing the instant release ramipril (R) substance joined to another tablet layer containing the dihydropyridine ER (D) preparation resulting in a multiple layer tablet. The two tablet layers can be joined directly to each other or via one or more intermediate layers (L).

EXAMPLE 1

Shown below are the pharmacokinetics of ramiprilat on treatment day 7 following once daily administration of the present invention according to Example 12 and a free monotherapy ramipril tablet (B), both given at 5 mg dosages, in 18 healthy volunteers. $C_{max}$ is the peak plasma concentration and $t_{max}$ is the time after administration the peak concentration was attained. $C_{min}$ is the lowest plasma concentration during the period. AUC is the area under the plasma concentration curve. SD is the standard deviation. p-values greater than 0.05 mean that there is no statistical significance in the quotient or the difference.

|                |      | Treatment |       |            |
|----------------|------|-----------|-------|------------|
| Parameter      |      | A         | B     | Comparison |
| $C_{max}$ (nmol/l) | mean | 23.8      | 24.2  | A/B        |
|                | SD   | 13.8      | 12.2  | p = 0.57   |
| $t_{max}$ (h)  | mean | 2.8       | 2.5   | A–B        |
|                | SD   | 1.1       | 0.9   | p = 0.35   |
| $C_{min}$ (nmol/l) | mean | 3.9       | 4.1   | A–B        |
|                | SD   | 1.2       | 0.9   | p = 0.64   |
| AUC (nmol · h/l) | mean | 211.1     | 213.3 | A/B        |
|                | SD   | 54.7      | 45.3  | p = 0.94   |

EXAMPLE 2

Shown below are the pharmacokinetics of felodipine on treatment day 7 following once daily administration of the present invention according to Example 12 and a free monotherapy felodipin tablet (B), both given at 5 mg dosages, in 18 healthy volunteers. $C_{max}$ is the peak plasma concentration and $t_{max}$ is the time after administration the peak concentration was attained. $C_{min}$ is the lowest plasma concentration during the period. AUC is the area under the plasma concentration curve. SD is the standard deviation. p-values greater than 0.05 mean that there is no statistical significance in the quotient or the difference.

|                |      | Treatment |       |            |
|----------------|------|-----------|-------|------------|
| Parameter      |      | A         | B     | Comparison |
| $C_{max}$ (nmol/l) | mean | 2.8       | 3.2   | A/B        |
|                | SD   | 1.0       | 1.3   | p = 0.18   |
| $t_{max}$ (h)  | mean | 4.6       | 4.6   | A–B        |
|                | SD   | 1.9       | 2.6   | p = 0.91   |
| $C_{min}$ (nmol/l) | mean | 0.9       | 0.9   | A–B        |
|                | SD   | 0.3       | 0.3   | p = 0.16   |
| AUC (nmol · h/l) | mean | 38.4      | 39.5  | A/B        |
|                | SD   | 14.5      | 12.9  | p = 0.33   |

EXAMPLE 3

The antihypertensive efficacy and tolerability of the combined fixed unit dosage form of felodipine ER and ramipril in doses of 5+5 mg and 2.5+2.5 mg were compared with those of individual monotherapies of felodipine ER 5 mg and ramipril 5 mg and with placebo in this double-blind, five armed parallel group multicentre study. Patients with primary hypertension whose supine diastolic blood pressure (DBP) was 95–110 mmHg inclusive at two separate occasions during the 4–6 week placebo run-in period were randomised to treatment either with felodipine ER-ramipril 5+5 mg (FR 5+5), felodipine ER-ramipril 2.5+2.5 mg (FR 2.5+2.5), felodipine ER 5 mg (F5), ramipril 5 mg (R5), or placebo.

Eleven-hundred and three (1103) patients were enrolled and nine-hundred and thirty-nine (939) patients from six countries (Australia, Canada, Denmark, Italy, New Zealand and Sweden) were randomised into this study. Eight-hundred and seventy (870) patients completed the study. In the analyses 518 males and 421 females with a mean age of 57 years, ranging from 24 to 86 years, were included.

Supine diastolic blood pressure (DBP) and supine systolic blood pressure (SBP) were measured 4 hours and 24 hours post dose at randomisation (baseline) and after 11 and 12 weeks of treatment.

Mean reduction in supine DBP and SBP from baseline to average of 11 and 12 weeks treatment (p-values less than 0.05 are statistically significant.)

Supine DBP (mm Hg)

| Administered agent | 4 hours | 24 hours |
|--------------------|---------|----------|
| Placebo            | −6.5    | −5.9     |
| FR 2.5 + 2.5       | −12.4   | −10.1    |
| FR 5 + 5           | −14.0   | −11.5    |
| F5                 | −11.4   | −9.4     |
| R5                 | −8.9    | −7.6     |

Supine SBP (mm Hg)

| Administered agent | 4 hours | 24 hours |
|--------------------|---------|----------|
| Placebo            | −6.8    | −5.6     |
| FR 2.5 + 2.5       | −17.9   | −14.2    |
| FR 5 + 5           | −20.1   | −14.8    |
| F5                 | −13.3   | −11.9    |
| R5                 | −12.1   | −8.6     |

All active treatments gave a statistically significant reduction in supine DBP (24 hours and 4 hours post dose) from baseline to the average of 11 to 12 weeks of treatment compared with placebo.

Mean differences in change (from baseline to average 11 to 12 weeks) in blood pressure. Comparison between combination treatments and placebo.

|  | Supine DBP | | | | Supine SBP | | | |
|---|---|---|---|---|---|---|---|---|
| Comparison | 24-hr | p-value | 4-hr | p-value | 24-hr | p-value | 4-hr | p-value |
| FR 2,5 + 2,5 vs placebo | −4.5 | <0.001 | −6.6 | <0.001 | −9.0 | <0.001 | −13.2 | <0.001 |
| FR 5 + 5 vs placebo | −6.0 | <0.001 | −8.0 | <0.001 | −9.6 | <0.001 | −15.0 | <0.001 |

Both treatments with combined fixed unit dosage forms given once daily to hypertensive patients gave a statistically significant reduction in both supine systolic and diastolic blood pressure compared to placebo, both at peak (4 hours post dose intake) and at trough (24 hours post dose intake). Mean differences in change (from baseline to average 11 to 12 weeks) in supine blood pressure. Comparison between treatments.

|  | Supine DBP | | | | Supine SBP | | | |
|---|---|---|---|---|---|---|---|---|
| Comparison | 24-hr | p-value | 4-hr | p-value | 24-hr | p-value | 4-hr | p-value |
| FR 5 + 5 vs F5 | −1.9 | 0.015 | −2.8 | 0.004 | −1.9 | 0.198 | −7.3 | <0.001 |
| FR 5 + 5 vs R5 | −3.9 | <0.001 | −5.7 | <0.001 | −6.9 | <0.001 | −8.5 | <0.001 |
| FR 2.5 + 2.5 vs F5 | −0.4 | 0.617 | −1.3 | 0.166 | −1.3 | 0.379 | −5.5 | 0.001 |
| FR 2.5 + 2.5 vs R5 | −2.4 | 0.003 | −4.2 | <0.001 | −6.3 | <0.001 | −6.7 | <0.001 |

The treatments with combined fixed unit dosage forms also gave a significantly greater reduction in both supine systolic and diastolic blood pressure than the individual monotherapies.

Furthermore, the low dose combination is equally (compared to felodipine) or more (compared to ramipril) effective in reducing supine diastolic and systolic blood pressure than double the dose of the individual monotherapies.

Similar results were obtained in the standing position indicating no orthostatic effects with any of the treatments. Most Common Adverse Events (% of patients)

|  | N = 187 Plac | N = 186 FR2.5 + 2.5 | N = 190 FR5 + 5 | N = 188 F5 | N = 188 R5 |
|---|---|---|---|---|---|
| Headache | 9.1 | 5.9 | 7.4 | 6.9 | 5.9 |
| Dizziness | 5.3 | 4.3 | 3.2 | 5.3 | 6.4 |
| Fatigue | 1.6 | 1.1 | 2.6 | <1.0 | 3.2 |
| Nausea | 2.7 | 1.6 | 1.1 | 1.6 | 3.2 |
| Oedema peripheral | 3.7 | 3.8 | 4.7 | 5.9 | 1.6 |
| Feeling warmth/Flush | <1.0 | 3.8 | 2.6 | 7.4 | 2.7 |
| Coughing | 2.7 | 5.9 | 7.4 | 4.8 | 10.6 |

Both therapies with combined fixed unit dosage forms were very well tolerated. The number of patients with adverse events and number of patients with adverse events causing stop of therapy in the fixed combination groups were comparable to that of placebo.

The incidence of the most common adverse event observed during administration of an ACE inhibitor (dizziness, headache, fatigue, nausea and coughing) and during administration of dihydropyridine calcium antagonists (increased heart rate, flushing, peripheral oedema, headache and dizziness) tended to be lower during therapy with combined fixed unit dosage forms than during therapy with the individual monotherapies. Above all, this is evident for the most bothersome adverse events with ACE inhibitors, coughing, and dihydropyridine calcium antagonists, peripheral oedema and flush.

EXAMPLE 4

Shown below are the results of a clinical study evaluating efficacy and tolerability of a combined fixed unit dosage form of felodipine ER and ramipril in the dose 2.5+2.5 mg (FR 2.5+2.5) in comparison with the individual monotherapies ramipril 2.5 mg (R 2.5) and felodipine ER 2.5 mg (F 2.5) given once daily. The study was of a double-blind, multicentre, 3-armed parallel group design. Similar inclusion criteria as in the study of Example 1 were used and treatment length 12 weeks. About 600 patients completed the study. The results are from measurement of blood pressures 24 hours post administration.

Mean reduction in supine DBP and SBP from baseline to 12 weeks (Pressures in mm Hg). Supine BP measured at 24 hours.

| Administered agent | Supine DBP | Supine SBP |
|---|---|---|
| FR 2.5 + 2.5 | −12.0 | −15.5 |
| F 2.5 | −9.6 | −12.0 |
| R 2.5 | −9.8 | −11.3 |

-continued

Adjusted mean difference in change from baseline to 12 weeks.
Supine BP measured at 24 hours.

|  | Supine DBP | | Supine SBP | |
| --- | --- | --- | --- | --- |
| Comparison | 24 hr | p-value | 24 hr | p-value |
| FR 2.5 + 2.5 vs F2.5 | −2.4 | 0.01 | −4.0 | 0.02 |
| FR 2.5 + 2.5 vs R2.5 | −1.6 | 0.07 | −3.9 | 0.02 |

Most Common ADEs (% of patients)

|  | N = 216 FR 2.5 + 2.5 | N = 213 F 2.5 | N = 213 R 2.5 |
| --- | --- | --- | --- |
| Headache | 5.1 | 5.6 | 4.2 |
| Back pain | 3.7 | 3.8 | 6.6 |
| Coughing | 6.0 | 1.4 | 5.2 |
| Vasodilatation | 3.7 | 3.3 | 1.9 |
| Infection | 1.9 | 3.3 | 2.3 |
| Peripheral oedema | 2.3 | 3.8 | 0.9 |
| Dizziness | 2.3 | 1.9 | 2.3 |

EXAMPLE 5

Capsule containing ramipril 2.5 mg on a carrier and a felodipine 5.0 mg compressed unit. Following unit ramipril is released quickly ("instant release") and felodipine is released during an extended period ("extended release").

Dissolution of ramipril/felodipine in vitro was tested in 500 ml of a 0.1 M phosphate buffer pH 6.5 with addition of 0.4% of cetyl trimethyl ammonium bromide (CTAB). USP dissolution apparatus No. 2 (paddle) equipped with stationary baskets, operated at 100 rpm was used. Release figures, in percent, denote average values and within brackets minimum—maximum values. 6 capsules were tested. For the composition of the capsule, see Example 9.

| Time (h) | Ramipril | Felodipine |
| --- | --- | --- |
| 0.5 | 102 (100–103) | not determined |
| 1 | not determined | 11 (11–13) |
| 4 | not determined | 61 (58–64) |
| 7 | not determined | 101 (99–104) |

EXAMPLE 6

Shown below is the dissolution of ramipril/felodipine in vitro from a coated tablet containing 2.5 mg/5 mg respectively of the active substances tested in 500 ml of a 0.1 M phosphate buffer pH 6.5 with addition of 0.4% of cetyl trimethyl ammonium bromide (CTAB). USP dissolution apparatus No. 2 (paddle) equipped with stationary baskets, operated at 100 rpm, was used. Release figures in percent, denote average value and within brackets minimum—maximum values. 6 tablets were tested. For the composition of the tablet, see Example 10.

| Time (h) | Ramipril | Felodipine |
| --- | --- | --- |
| 0.5 | 103 (99–107) | not determined |
| 1 | not determined | 9 (8–9) |
| 4 | not determined | 53 (50–56) |
| 7 | not determined | 90 (86–94) |

EXAMPLE 7

Shown below is the dissolution of ramipril/felodipine in vitro from a layered tablet containing 2.5 mg/2.5 mg respectively of the active substances in 500 ml of a 0.1 M phosphate buffer pH 6.5 with addition of 0.4% of cetyl trimethyl ammonium bromide (CTAB). USP dissolution apparatus No. 2 (paddle) equipped with stationary baskets, operated at 100 rpm, was used. Release figures, in percent denote average value and figures within brackets denote minimum—maximum values. 6 tablets were tested. For the composition of the tested tablet, see Example 11.

| Time (h) | Ramipril | Felodipine |
| --- | --- | --- |
| 0.5 | 97 (90–103) | not determined |
| 1 | not determined | 8 (6–9) |
| 4 | not determined | 54 (51–56) |
| 7 | not determined | 92 (89–94) |

EXAMPLE 8

Show below is the dissolution of ramipril/felodipine in vitro from a layered tablet containing 5 mg/5 mg respectively of the active substances tested in 500 ml of a 0.1 M phosphate buffer pH 6.5 with addition of 0.4% of cetyl trimethyl ammonium bromide (CTAB). USP dissolution apparatus No. 2 (paddle) equipped with stationary baskets, operated at 100 rpm, was used. Release figures in percent, denote average values and figures within brackets denote minimum—maximum values. 6 tablets were tested. For the composition of the tested tablet, see Example 12.

| Time (h) | Ramipril | Felodipine |
| --- | --- | --- |
| 0.5 | 94 (89–100) | not determined |
| 1 | not determined | 12 (12–13) |
| 4 | not determined | 60 (58–61) |
| 7 | not determined | 95 (93–96) |

EXAMPLE 9

A capsule containing ramipril 2.5 mg on a carrier and a felodipine 5.0 mg compressed unit. Was prepared Ramipril is released quickly ("instant release") and felodipine is released during an extended period ("extended release").

The felodipine tablet core was constructed according to the hydrophilic gel matrix principle described in "Hydrophilic Matrix Sustained Release Systems Based on Polysaccharide Carriers" by Colin D. Melia, in Critical Reviews in Therapeutic Drug Carrier Systems, 8(4): 395–421(1991) in the following way: Two different granulating solutions (I and II) were prepared and the solutions were used for granulating the powder mass (III).

|  | mg/tablet |
| --- | --- |
| Solution I | |
| Felodipine | 5.00 |
| Polyoxyl 40 hydrogenated castor oil | 12.50 |
| Propyl gallate | 0.060 |
| Ethanol | 30.00 |
| Solution II | |
| Polyvinyl pyrrolidone | 24.00 |
| Ethanol | 300.0 |
| Powders in granulate III | |
| Hydroxypropyl methylcellulose | 200.00 |
| Sodium Aluminium silicate | 94.00 |
| Lactose | 56.00 |
| Microcrystalline cellulose | 6.00 |
| Hydroxypropyl methylcellulose | 30.00 |
| Sodium stearylfumarate | 8.60 |

The powder mixture was moistened with Solution I while mixing to homogeneity. Then Solution II was added and mixing was continued until homogeneity. Drying of the granulate was performed in a drying oven.

The dry granulate was milled using a Frewitt oscillating granulator. After milling the granulate was mixed with additionally 30 mg per tablet of hydroxypropyl methyl cellulose (HPMC) until homogeneity and then lubricated with sodium stearyl fumarate. The final mixing was continued for 3 minutes. Compression was performed in a Korsch Pharmapress 100 with 7×13 punches (scored). Obtained tablet hardness measured over the longest axis was greater than 20 kP.

The ramipril carrier was manufactured in the following way:

| Coating solution | |
| --- | --- |
| Ramipril | 3.33 g |
| HPMC | 10.00 g |
| Acetic acid 0.01 M | 200 g |
| EtOH | 200 g |
| Core | |
| Non-Pareille inert core | 210 g |
| (According to USP monograph for "Sugar Spheres") | |
| Equipment | |
| Fluid bed (Wurster equipped), | |
| Spray Nozzle: Schlick | |
| Insert tube diameter 50 mm, length 60 mm | |

The coating process resulted in beads having a ramipril content of 13.5 mg/g. One of the tablets from the above was filled in a hard gelatin capsule, size 00, together with 185 mg of the ramipril containing beads.

| Properties of the obtained capsules | |
| --- | --- |
| Capsule weight | 747 mg |
| Felodipine content | 5.0 |
| Ramipril content | 2.4 mg/capsule |

EXAMPLE 10

A tablet containing ramipril in the coat and felodipine in the tablet core. Was prepared Ramipril is released instantly whereas felodipine is released during an extended period.

The felodipine tablet core was constructed according to the hydrophilic gel matrix principle (See reference example 7) in the following way: Two different granulating solutions (I and II) were made, and these were used to granulate the powder mass (III).

|  | mg/tablet |
| --- | --- |
| Solution I | |
| Felodipine | 5.00 |
| Polyoxyl 40 hydrogenated castor oil | 5.00 |
| Propyl gallate | 0.060 |
| Ethanol | 30.00 |
| Solution II | |
| Hydroxypropyl cellulose | 10.00 |
| Ethanol | 160.00 |
| Powders III | |
| Hydroxypropyl methylcellulose | 100.00 |
| Sodium Aluminium silicate | 47.00 |
| Lactose | 28.00 |
| Microcrystalline cellulose | 3.00 |
| Sodium stearylfumarate | 4.20 |

The powder mixture was moistened with Solution I while mixing to homogeneity. The Solution II was added and mixing continued to homogeneity. Drying of the granulate was performed in a drying oven.

The dry granulate was milled using a Frewitt oscillating granulator. After milling, the granulate was lubricated with sodium stearyl fumarate and the final mixing was continued for 3 minutes. Tabletting was performed on a tabletting machine using 9 mm circular concave punches. Obtained tablet hardness was approximately 7–8 kP measured with a Schleuniger hardness tester.

The felodipine tablets obtained according to the above were used as cores in a coating process applying a coating layer comprising ramipril and, as a binder, hydroxypropyl methyl cellulose (HPMC) 6 cps, dissolved in a mixture of alcohol and an acetic acid water solution.

The tablet cores were coated in the following way:

| Coating solution | |
| --- | --- |
| Acetic acid sol. 0.01 M | 200 g |
| Ethanol | 200 g |
| HPMC 6 cps | 10 g |
| Ramipril | 3.46 g |
| Cores | |
| Felodipine ER tablets 5 mg, diameter 9 mm (1000 tablets) | 206 g |

Equipment

Fluid bed (Wurster equipped)

Spray nozzle: Schlick

Insert tube diameter 50 mm, length 60 mm

The HPMC was dissolved in a mixture of the acetic acid water solution and the ethanol, then the ramipril powder was dissolved in this solution. The solution was sprayed onto the tablets using the equipment and under the conditions specified above. Coating may, alternatively, be performed in other conventional equipment, e.g. Accela Coata or coating pans.

| Properties of the obtained tablets | |
|---|---|
| Tablet weight | 216 mg/tablet |
| Felodipine content | 4.9 mg/tablet |
| Ramipril content | 2.4 mg/tablet |

EXAMPLE 11

Combined instant release ramipril and extended release felodipine layered tablets 2.5 mg/2.5 mg. Composition.

| Component | mg/tablet |
|---|---|
| Ramipril layer | |
| Ramipril | 2.5 |
| Hydroxypropyl methylcellulose | 0.4 |
| Lactose | 24.0 |
| Maize starch 1500 | 48.8 |
| Microcrystalline cellulose | 24.0 |
| Sodium stearyl fumarate | ≦1.0 |
| Water purified | q.s. |
| Felodipine layer | |
| Felodipine | 2.5 |
| Hydroxypropylcellulose | 10.0 |
| Hydroxypropyl methylcellulose | 100 |
| Lactose | 28.0 |
| Microcrystalline cellulose | 3.0 |
| Polyoxyl 40 hydrogenated castor oil | 2.5 |
| Propyl gallate | 0.06 |
| Sodium aluminium silicate | 47.0 |
| Sodium stearyl fumarate | ≦6 |
| Ethanol | q.s. |
| Coating layer | |
| Colour iron oxide | about 0.3 |
| Hydroxypropyl methylcellulose | 7.4 |
| Paraffin | about 0.1 |
| Polyethylene glycol | 1.9 |
| Titanium dioxide | 0.8 |
| Water purified | about 64 |

Ramipril was granulated with hydroxypropyl methylcellulose in purified water. The dried material was classified and mixed with lactose, maize starch and microcrystalline cellulose. Final mixing was made with sieved sodium stearyl fumarate. The felodipine granulate was manufactured separately according to the procedure described in Example 8. The two granulates were then fed into a layer press equipped with two filling stations and compressed into tablets.

The tablets were finally coated with an outer coating layer using conventional equipment.

EXAMPLE 12

Combined instant release ramipril and extended release felodipine layered tablets 5 mg/5 mg were prepared. The compositions of the layers are set forth below.

| Component | mg/tablet |
|---|---|
| Ramipril layer | |
| Ramipril | 5.0 |
| Hydroxypropyl methylcellulose | 0.9 |
| Lactose | 23.5 |

| Component | mg/tablet |
|---|---|
| Maize starch 1500 | 46.8 |
| Microcrystalline cellulose | 23.5 |
| Sodium stearyl fumarate | ≦1.0 |
| Water purified | q.s. |
| Felodipine layer | |
| Felodipine | 5.0 |
| Hydroxypropylcellulose | 10.0 |
| Hydroxypropyl methylcellulose | 100.0 |
| Lactose | 28.0 |
| Microcrystalline cellulose | 3.0 |
| Polyoxyl 40 hydrogenated castor oil | 5.0 |
| Propyl gallate | 0.06 |
| Sodium aluminium silicate | 47.0 |
| Sodium stearyl fumarate | ≦6 |
| Ethanol | q.s. |
| Coating layer | |
| Colours, iron oxides | about 0.3 |
| Hydroxypropyl methylcellulose | 7.5 |
| Paraffin | about 0.1 |
| Polyethylene glycol | 1.9 |
| Titanium dioxide | 0.8 |
| Water purified | about 65 |

For the manufacturing process see example 11.

We claim:

1. A pharmaceutical preparation for oral administration comprising a combination of
    a) the ACE inhibitor ramipril, or a pharmaceutically acceptable salt thereof, and
    b) a dihydropyridine compound selected from the group consisting of felodipine, nitrendipine, nifedipine, and lacidipine, or a pharmaceutically acceptable salt thereof, wherein
        1) ramipril is in instant release form,
        2) the dihydropyridine compound is in extended release (ER) form and
        3) the combination is in a solid fixed-unit dosage form.

2. A pharmaceutical preparation according to claim 1 wherein the dihydropyridine compound is felodipine or a pharmaceutically acceptable salt thereof.

3. A pharmaceutical preparation according to claim 1 wherein the dihydropyridine compound is nitrendipine or a pharmaceutically acceptable salt thereof.

4. A pharmaceutical preparation according to claim 1 wherein the dihydropyridine compound is nifedipine or a pharmaceutically acceptable salt thereof.

5. A pharmaceutical preparation according to claim 1 wherein the dihydropyridine compound is lacidipine or a pharmaceutically acceptable salt thereof.

6. A pharmaceutical preparation according to any one of claims 1 to 5 wherein the amount of ramipril or a pharmaceutically acceptable salt thereof is 1 to 10 mg and the amount of the dihydropyridine compound or a pharmaceutically acceptable salt thereof is 1 to 70 mg per dosage unit.

7. A pharmaceutical preparation according to claim 6 wherein the amount of ramipril or a pharmaceutically acceptable salt thereof is 1 to 5 mg and the amount of the dihydropyridine compound or a pharmaceutically acceptable salt thereof is 1 to 60 mg per dosage unit.

8. A pharmaceutical preparation according to claim 2 wherein the amount of each of ramipril or a pharmaceutically acceptable salt thereof and felodipine or a pharmaceutically acceptable salt thereof is 1–5 mg per dosage unit.

9. A pharmaceutical preparation according to claim 2 wherein the amount of each of ramipril or a pharmaceutically acceptable salt thereof and felodipine or a pharmaceutically acceptable salt thereof is 1–3 mg per dosage unit.

10. A pharmaceutical preparation according to claim 8 wherein the dosis quotient of the components is 1:1.

11. A pharmaceutical preparation according to claim 9 wherein the dosis quotient of the components is 1:1.

12. A pharmaceutical preparation according to any one of claims 1 to 5, 8 to 10, or 11 wherein the solid fixed-unit dosage form is a capsule.

13. A pharmaceutical preparation according to any one of claims 1 to 5, 8 to 10, or 11 wherein the solid fixed-unit dosage form is a tablet.

14. A pharmaceutical preparation according to any one of claims 1 to 5, 8 to 10, or 11 wherein the ramipril component is included in a coating layer which is surrounding the dihydropyridine ER component.

15. A pharmaceutical preparation according to claim 13 wherein the dihydropyridine ER component is in a tablet layer which is joined to another tablet layer containing the ramipril component, or, optionally, wherein the dihydropyridine ER component is in a tablet layer which is joined, indirectly via one or more layers without active components, to another tablet layer containing the ramipril component.

16. A pharmaceutical preparation according to any one of claims 1 to 5, 8 to 10, or 11 wherein one of the components is contained in a smaller part which is contained in a larger, separate part containing the other component.

17. A process for the manufacture of a pharmaceutical preparation according to any one of claims 1 to 5, 8 to 10, or 11 wherein the ramipril and the dihydropyridine ER components are compressed into a tablet in a tabletting machine.

18. A process for the manufacture of a pharmaceutical preparation according to any one of claims 1 to 5, 8 to 10, or 11 wherein a tablet layer containing the ramipril component is joined to a tablet layer containing the dihydropyridine ER substance to produce a combined tablet.

19. A process according to claim 17 wherein the tablet product is coated with a pharmaceutically acceptable coating.

20. A process for the manufacture of a pharmaceutical preparation according to claim 12 wherein ramipril and an extended release form of dihydropyridine are enclosed into a capsule.

21. A method of preventing or treating hypertension in mammals comprising the administration of an effective amount of a pharmaceutical preparation according to any one of claims 1 to 5, 8 to 10, or 11 to a patient in need of such treatment.

22. A method of preventing or treating hypertension in mammals comprising the administration once per day of an effective amount of a pharmaceutical preparation according to any one of claims 1 to 5, 8 to 10, or 11 to a patient in need of such treatment.

23. A pharmaceutical preparation according to any one of claims 1 to 5, 8 to 10, or 11 wherein the ER formulation is comprised in a hydrophilic gel matrix.

24. A pharmaceutical preparation according to claim 6 wherein the ER formulation is comprised in a hydrophilic gel matrix.

25. A pharmaceutical preparation according to claim 6 wherein the solid fixed-unit dosage form is a capsule.

26. A pharmaceutical preparation according to claim 6 wherein the solid fixed-unit dosage form is a tablet.

27. A pharmaceutical preparation according to claim 6 wherein the ramipril component is included in a coating layer which is surrounding the dihydropyridine ER component.

28. A pharmaceutical preparation according to claim 14 wherein the dihydropyridine ER component is in a tablet layer which is joined to another tablet layer containing the ramipril component, or, optionally, wherein the dihydropyridine ER component is in a tablet layer which is joined, indirectly via one or more layers without active components, to another tablet layer containing the ramipril component.

29. A pharmaceutical preparation according to claim 26 wherein the dihydropyridine ER component is in a tablet layer which is joined to another tablet layer containing the ramipril component, or, optionally, wherein the dihydropyridine ER component is in a tablet layer which is joined, indirectly via one or more layers without active components, to another tablet layer containing the ramipril component.

30. A pharmaceutical preparation according to claim 27 wherein the dihydropyridine ER component is in a tablet layer which is joined to another tablet layer containing the ramipril component, or, optionally, wherein the dihydropyridine ER component is in a tablet layer which is joined, indirectly via one or more layers without active components, to another tablet layer containing the ramipril component.

31. A pharmaceutical preparation according to claim 6 wherein one of the components is contained in a smaller part which is contained in a larger, separate part containing the other component.

32. A process for the manufacture of a pharmaceutical preparation according to claim 6 wherein the ramipril and the dihydropyridine ER components are compressed into a tablet in a tabletting machine.

33. A process for the manufacture of a pharmaceutical preparation according to claim 6 wherein a tablet layer containing the ramipril component is joined to a tablet layer containing the dihydropyridine ER substance to produce a combined tablet.

34. A process according to claim 18 wherein the tablet product is coated with a pharmaceutically acceptable coating.

35. A process according to claim 32 wherein the tablet product is coated with a pharmaceutically acceptable coating.

36. A process according to claim 33 wherein the tablet product is coated with a pharmaceutically acceptable coating.

37. A process for the manufacture of a pharmaceutical preparation according to claim 25 wherein ramipril and an extended release form of dihydropyridine are enclosed into a capsule.

38. A method of preventing or treating hypertension in mammals comprising the administration of an effective amount of a pharmaceutical preparation according to claim 6 to a patient in need of such treatment.

39. A method of preventing or treating hypertension in mammals comprising the administration once per day of an effective amount of a pharmaceutical preparation according to claim 6 to a patient in need of such treatment.

* * * * *